United States Patent [19]

Butler

[11] 4,179,506

[45] Dec. 18, 1979

[54] NEW PYRIDOBENZODIOXIN COMPOUNDS AND METHODS FOR THEIR PRODUCTION

[75] Inventor: Donald E. Butler, Ann Arbor, Mich.

[73] Assignee: Warner-Lambert Company, Morris Plains, N.J.

[21] Appl. No.: 960,252

[22] Filed: Nov. 13, 1978

[51] Int. Cl.$^2$ .................. A61K 31/535; C07D 491/04
[52] U.S. Cl. ...................................... 424/256; 546/90; 546/290
[58] Field of Search ........................... 546/90; 424/256

[56] References Cited

U.S. PATENT DOCUMENTS 3,865,832  2/1975  Boschman et al. ............... 546/90 or

OTHER PUBLICATIONS

Chemical Abstracts, vol. 73, abst. No. 109766n (1970) (abst. of Crabb et al., J. Chem. Soc. D 1970, 1123-4).

Primary Examiner—John D. Randolph
Attorney, Agent, or Firm—Stephen Raines; David B. Ehrlinger; Frank S. Chow

[57] ABSTRACT

Pyridobenzodioxin compounds, which are useful as pharmacological agents, especially as agents for the treatment of senility and reversal of amnesia, and methods for their preparation are disclosed. Pharmaceutical compositions containing said compounds and methods for using said compositions in treating senility and reversal of amnesia are also taught.

10 Claims, No Drawings

NEW PYRIDOBENZODIOXIN COMPOUNDS AND METHODS FOR THEIR PRODUCTION

SUMMARY AND DETAILED DESCRIPTION

The present invention relates to new pyrido[2,3-B][1,4]-benzodioxin and pyrido[3,4-B][1,4]benzodioxan and the corresponding N-oxides. More particularly, the invention relates to new compounds of the formula

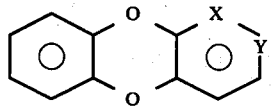

and to a method for the production of the foregoing compounds; where X is N or N→O and Y is CH or X is CH and Y is N or N→O and pharmaceutically acceptable acid addition salts of compounds wherein X is N or Y is N.

The term "pharmaceutically-acceptable salt" is intended to mean a relatively non-toxic acid addition salt, such as the hydrochloride, sulfate [two equivalents of pyridinium compound would be coupled to a sulfate moiety], acetate, benzoate, etc.

In accordance with the invention, the foregoing compounds of formula I wherein X is N and Y is CH can be prepared by ring closing a compound of the formula

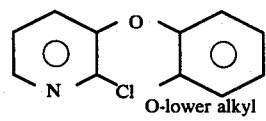

while compounds of formula I wherein X is CH and Y is N are prepared by ring closing a compound of the formula

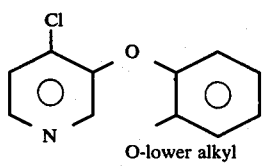

III

The pharmaceutically-acceptable salts are prepared by adjusting the pH.

The term "lower alkyl" is intended to mean an alkyl group of from one to four carbon atoms, such as methyl, ethyl, t-butyl, etc.

The reaction is carried out in the presence of an excess of pyridine hydrochloride which also acts as the solvent.

The reaction is carried out at a temperature range of 100° C. to 210° C. for periods of from one to 72 hrs, preferably 200° to 210° C for from one to two hrs.

The product may be isolated as the free base by sublimation or crystallization or as an acid addition salt by suitable adjustment of pH.

The necessary starting material of formulae II and III are prepared by treating a compound of formula

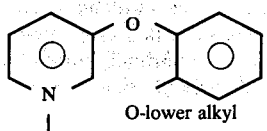

IV with POCl$_3$.

The above chlorination reaction is carried out generally in an excess of phosphorous oxychloride in a chlorinated hydrocarbon solvent at about the reflux temperature of the phosphorous oxychloride for about four hours and separating the isomers, preferably by chromatography.

The compounds of the invention wherein X is N→O or Y is N→O are prepared by oxidizing the corresponding compound wherein X is N or Y is N using standard oxidation methods.

Any excess of an oxidizing agent, such as 3 to 30% hydrogen peroxide in water, 5 to 40% peracetic acid in acetic acid, perbenzoic acid, pertrifluoroacetic acid, perphthalic acid and m-chloroperbenzoic acid may be used. Preferred is 40% peracetic acid in acetic acid. Generally an excess of oxidizing agent is employed.

The reaction may be carried out in water or most any organic solvent which will not undergo oxidation itself under the conditions of this reaction. This would include; glacial acetic acid, or any other lower alkanoic acid, mixtures of water and acetic acid, halogenated hydrocarbons, such as dichloromethane, chloroform or tetrachloroethane. Preferred is glacial acetic acid or dichloromethane.

The reaction is carried out at a temperature range of 25° to 100° C. for periods of from one to 96 hrs, preferably 65° to 70° C. for about one hr or 40° C. for 96 hrs.

The product may be isolated by sublimation or crystallization.

The compounds of the invention may exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula I in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin, talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations.

The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

The compounds of formula I may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc.

The compounds of the invention are new chemical compounds of value as pharmacological agents. More specifically, they are agents which are potentially useful in treating patients suffering from senility. The compounds also find use in the treatment of induced amnesia. The compounds of the invention generally would be administered to mammals in a dosage range of from about 0.014 to about 21.4 mg per kg of body weight per day, preferably 0.36 to 10.7 mg per kg per day. Thus 1 mg to 1500 mg, preferably 25 mg to 750 mg, are administered to a 70 kg host per day.

The effectiveness of the aforementioned compounds is determined by the following test. This test is designed to show the compound's ability to reverse amnesia produced by electroconvulsive shock.

One hundred male mice (Carworth, CF-1 strain, 19–21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assesed. Usually three doses of the chemical will be tested at a time.

One hour after the drum treatment, the mice are tested for memory of the painful foot shock received within the self-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | |
|---|---|
| 1) Ceiling Control Group: | Placebo |
| 2) Base Line Control Group: | Electroconvulsive shock, Placebo |
| 3) 1st Drug Dose Group: | Electroconvulsive shock, pyridobenzodioxin |
| 4) 2nd Drug Dose Group: | Electroconvulsive shock, pyridobenzodioxin |
| 5) 3rd Drug Dose Group: | Electroconvulsive shock, pyridobenzodioxin |

The percentage of amnesia reversal is determined as follows for each drum group:

$$\text{Percent amnesia reversal} = \frac{\text{Drug group} - \text{Base line control group}}{\text{Ceiling control group} - \text{Base line control group}} \times 100$$

The following criteria is used in interpreting the percent of amnesia reversal scores:

40 percent or more (active=A) 25 to 39 percent (borderline=C) and 0 to 29 percent (inactive=N). The duration of the electroconvulsive shock can be varied making the test more or less difficult for a compound to demonstrate an A or C rating. Thus a compound with activity in senile patients and in patients with early memory defects, Piracetam ® [Acta Psychiat. Scand, 54, 150 (1976)], has been administered in this test using the above methodology and 0.2 second and 0.5 second electroconvulsive shock and gave the following results.

| Piracetam ® (mg/kg) | 0.2 sec ECS | 0.5 sec ECS |
|---|---|---|
| 80 | C | N |
| 20 | A | N |
| 5 | C | N |

The inverted U shaped dose response curve is typical of this type of agent.

The following table reports the results for certain compounds of the invention:

Table 1

| | LMC Test | | | | | |
| | Dose Levels (mg/kg) | | | | | |
| Compound | 1.25 | 2.5 | 5.0 | 10. | 20 | 80 |
|---|---|---|---|---|---|---|
| Example 1 | N | C | A | C | N | N |
| Example 2 | | | N | | N | A |
| Example 3 | | | N | | N | A |

| Table 1-continued | | | | | | |
|---|---|---|---|---|---|---|
| | LMC Test | | | | | |
| | Dose Levels (mg/kg) | | | | | |
| Compound | 1.25 | 2.5 | 5.0 | 10. | 20 | 80 |
| Example 4 | | | N | | C | A |

The invention is illustrated by the following examples.

EXAMPLE 1 pyrido[2,3-B][1,4]benzodioxin

Anhydrous pyridine hydrochloride is prepared by distillation to a temperature of 220° C. from a mixture of 42 g of pyridine and 50 ml of concentrated hydrochloric acid. Under a nitrogen atmosphere, the pyridine hydrochloride is allowed to cool to 100° C. and 5 g of 2-chloro-3-(2-methoxyphenoxy)pyridine is added and the mixture is refluxed 1 hour. The mixture is cooled and 200 ml of water is added. The mixture is extracted with 250 ml diethyl ether and the extracts are washed with 10 ml of concentrated ammonium hydroxide. The ether layer is dried and evaporated to yield the pyrido[2,3-B][1,4]benzodioxin, mp 95°–97° C., after sublimation at 0.1 mm pressure.

EXAMPLE 2 pyrido[2,3-B][1,4]benzodioxin 1-oxide

A solution of 32 g of pyrido[2,3-B][1,4]benzodioxin in 100 ml of glacial acetic acid is treated with 36 g of 40% peracetic acid in acetic acid in four equal portions. After the fourth portion is added, the mixture is heated at 70° C. for 10 minutes. Another 4 g of 40% peracetic acid in acetic acid is added and the temperature is maintained at 70° C. for 10 minutes and then heated to reflux for 10 minutes. The mixture is concentrated at reduced pressure, 100 ml of isopropanol is added and the mixture is concentrated again. The resulting oil is dissolved in 700 ml of dichloromethane and the organic layer is washed with excess cold 25% sodium hydroxide solution. The organic layer is dried and evaporated to yield the pyrido[2,3-B][1,4]-benzodioxin 1-oxide, mp 223°–226° C. after recrystallization from acetonitrile.

EXAMPLE 3 pyrido[3,4-B][1,4]benzodioxin

By substituting 5 g of 4-chloro-3-(2-methoxyphenoxy)pyridine for the 2-chloro-3-(2-methoxyphenoxy)pyridine of Example 1, the product is pyrido[3,4-B][1,4]benzodioxin, mp 102°–108° C. after sublimation at 0.1 mm.

EXAMPLE 4 pyrido[3,4-B][1,4]benzodioxin-2 oxide

A solution of 3.5 g of pyrido[3,4-B][1,4]benzodioxin in 40 ml of dichloromethane is treated with 4.04 g of 85% m-chloroperbenzoic acid. The mixture is refluxed with stirring for 4 days. The mixture is diluted with 250 ml of dichloromethane and washed with excess 25% sodium hydroxide solution. The organic layer is dried and evaporated to yield pyrido[3,4-B][1,4]-benzodioxin-2 oxide, mp 232°–233° C. dec.

EXAMPLE 5

Pharmaceutical Composition containing pyrido-[2,3-B][1,4]benzodioxin

| Ingredient | Quantity |
|---|---|
| Pyrido[2,3-B] [1,4]benzodioxin | 150 g |
| Lactose | 1038 g |
| Corn Starch | 39 g |
| Hydroxypropyl cellulose | 30 g |
| Magnesium stearate | 7 g |
| Ethanol-water 50:50 | qs |

The pyrido[2,3-B][1,4]benzodioxin, lactose and hydroxypropyl cellulose are blended and granulated with 50:50 ethanol-water. The wet granulation is blended with the magnesium stearate and the corn starch, and the mixture is compressed into 225 mg tablets using 11/32 inch standard concave punches. Yield equals approximately 6,000 tablets each containing 25 mg of pyrido[2,3-B][1,4]benzodioxin.

Intermediates for Examples 1 and 3

2-Chloro-3-(2-methoxyphenoxy)pyridine,
4-chloro-3-(2-methoxyphenoxy)pyridine,
6-chloro-3-(2-methoxyphenoxy)pyridine A solution of 135 g of 3-(2-methoxyphenoxy)pyridine 1-oxide [J. Med. Chem., 14, 575 (1971)] in 150 ml of dichloromethane is added dropwise to 480 g of refluxing phosphorous oxychloride allowing the dichloromethane to distill. The mixture is refluxed 4 hours, cooled and concentrated at reduced pressure. The oil is dissolved in 1 L of dichloromethane and is washed with ice cold concentrated ammonium hydroxide, dried and distilled to yield the mixture of isomeric chlorinated 3-(2-methoxyphenoxy)pyridines. The isomeric mixture is chromatographed over 2.5 kg of silica gel in toluene. The 6-chloro-3-(2-methyoxyphenoxy)pyridine is eluted by the toluene, 2-chloro-3-(2-methoxyphenoxy)pyridine is eluted using 1% methanol-toluene, mp 71°–74° C. after evaporation of the solvent at reduced pressure and trituration with petroleum ether. The final eluate contains the 4-chloro-3-(2-methoxyphenoxy)pyridine.

I claim:

1. A compound of the formula

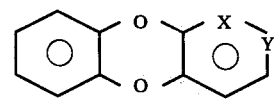

where X is N or N→O and Y is CH or X is CH and Y is N or N→O and pharmaceutically-acceptable acid addition salts of compounds where X is N or Y is N.

2. A compound of claim 1 having the name pyrido[2,3-B][1,4]benzodioxin.

3. A compound of claim 1 having the name pyrido[2,3-B][1,4]benzodioxin 1-oxide.

4. A compound of claim 1 having the name pyrido[3,4-B][1,4]benzodioxin.

5. A compound of claim 1 having the name pyrido[3,4-B][1,4]benzodioxin-2 oxide.

6. A pharmaceutical composition comprising a compound of claim 1 and a pharmaceutical carrier.

7. A method for treating senility which comprises administering the composition of claim 6.

8. A method for reversing amnesia which comprises administering the composition of claim 6.

9. A method for preparing a compound of claim 1 wherein N is in the form of a free amine which comprises ring closing a compound of the formulae

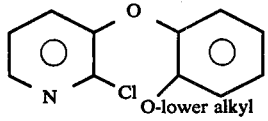

or

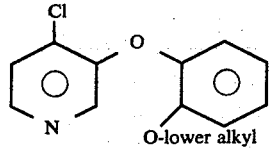

and adjusting the pH.

10. A method for preparing a compound of claim 1 wherein N is in the form of an N-oxide which comprises oxidizing the corresponding free base.

* * * * *